(12) United States Patent
Nagae (10) Patent No.: US 11,723,539 B2
(45) Date of Patent: Aug. 15, 2023

(54) PHOTOACOUSTIC SUBJECT INFORMATION ACQUISITION APPARATUS FOR IMAGING A SUBJECT BY MOVING PROBE TO CIRCULATE ALONG A COMMON CIRCULATING PATH

(71) Applicant: CANON KABUSHIKI KAISHA, Tokyo (JP)

(72) Inventor: Kenichi Nagae, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 1043 days.

(21) Appl. No.: 16/005,209

(22) Filed: Jun. 11, 2018

(65) Prior Publication Data

US 2018/0360322 A1    Dec. 20, 2018

(30) Foreign Application Priority Data

Jun. 16, 2017 (JP) .................................. 2017-118995

(51) Int. Cl.
*A61B 5/00* (2006.01)

(52) U.S. Cl.
CPC ............ *A61B 5/0095* (2013.01); *A61B 5/742* (2013.01); *A61B 5/4312* (2013.01); *A61B 5/708* (2013.01);
(Continued)

(58) Field of Classification Search
CPC ..... A61B 5/0095; A61B 5/742; A61B 5/7203; A61B 5/708; A61B 5/4312; A61B 2576/00; A61B 5/004; A61B 5/0064; A61B 5/0075
See application file for complete search history.

(56) References Cited

U.S. PATENT DOCUMENTS

| 2013/0217995 A1* | 8/2013 | Kruger | ................. | A61B 5/6835 600/407 |
| 2016/0192843 A1* | 7/2016 | Kruger | ................. | A61B 5/0095 600/407 |
| 2016/0213259 A1 | 7/2016 | Wanda | | |

FOREIGN PATENT DOCUMENTS

| CN | 102525550 A | 7/2012 |
| CN | 104586356 A | 5/2015 |

(Continued)

OTHER PUBLICATIONS

Paltauf et al (Artifact removal in photoacoustic section imaging by combining an integrating cylindrical detector with model-based reconstruction, Journal of Biomedical Optics 19(2), 026014 (Feb. 2014) (Year: 2014).*

*Primary Examiner* — Serkan Akar
(74) *Attorney, Agent, or Firm* — Canon U.S.A., Inc. IP Division (57) ABSTRACT

A subject information acquisition apparatus includes a light irradiation unit configured to irradiate a subject with light, a probe configured to detect an acoustic wave generated in the subject due to the irradiation of the light, a moving unit configured to change a relative position between the probe and the subject, and a control unit configured to control the moving unit to move the probe so that the probe makes a movement along a path a plurality of times. The moving unit is controlled so that the relative position of the probe with respect to the subject when the subject is irradiated with the light during a first movement along the path differs from the relative position of the probe with respect to the subject when the subject is irradiated with the light during a second movement along the path successively performed after the first movement along the path.

16 Claims, 8 Drawing Sheets

(52) U.S. Cl.
CPC ......... *A61B 5/7203* (2013.01); *A61B 2576/00* (2013.01)

(56) References Cited

FOREIGN PATENT DOCUMENTS

| | | |
|---|---|---|
| CN | 105054971 A | 11/2015 |
| CN | 106667442 A | 5/2017 |
| JP | 2016-137053 A | 8/2016 |
| JP | 2016-529061 A | 9/2016 |
| JP | 2017-038917 A | 2/2017 |
| WO | 2015/174085 A1 | 11/2015 |
| WO | 2016/047102 A1 | 3/2016 |
| WO | 2016/076244 A1 | 5/2016 |

* cited by examiner

FIG. 8 ic # PHOTOACOUSTIC SUBJECT INFORMATION ACQUISITION APPARATUS FOR IMAGING A SUBJECT BY MOVING PROBE TO CIRCULATE ALONG A COMMON CIRCULATING PATH

BACKGROUND

Technical Field

The present invention relates to an apparatus for detecting acoustic waves propagating from a subject and a method for controlling the apparatus.

Description of the Related Art

In photoacoustic wave acquisition for detecting photoacoustic waves generated in a subject, it is known to relatively move a probe with respect to the subject while detecting photoacoustic waves. Artifacts occurring in an image generated based on the photoacoustic images can be reduced by detecting the photoacoustic waves at different positions. Japanese Patent Application Laid-Open No. 2016-137053 discusses the detection of photoacoustic waves while moving a probe to trace a spiral or circumferential trajectory. The same region of interest can be measured a plurality of times in succession by repeating measurement while moving the probe to circulate along the trajectory a plurality of times.

SUMMARY

The present inventor has found that according to Japanese Patent Application Laid-Open No. 2016-137053, if the probe is moved to circulate along the same path a plurality of times and acoustic waves are detected at the same positions in consecutive rounds, the reduction of artifacts can be insufficient due to the fixed positions of detection of the acoustic waves.

According to an aspect of the present invention, a subject information acquisition apparatus includes a light irradiation unit configured to irradiate a subject with light, a probe configured to detect an acoustic wave generated in the subject due to irradiation with the light, a moving unit configured to change a relative position between the probe and the subject, and a control unit, wherein the control unit is configured to control the moving unit to move the probe so that the probe makes a circulating movement a plurality of times, and wherein the moving unit is controlled so that the relative position of the probe with respect to the subject when the subject is irradiated with the light during a first circulating movement differs from the relative position of the probe with respect to the subject when the subject is irradiated with the light during a second circulating movement successively performed after the first circulating movement.

Further features of the present invention will become apparent from the following description of exemplary embodiments with reference to the attached drawings.

DESCRIPTION OF THE EMBODIMENTS

Exemplary embodiments will be described in detail below with reference to the drawings. Each of the embodiments of the present invention described below can be implemented solely or as a combination of a plurality of the embodiments or features thereof where necessary or where the combination of elements or features from individual embodiments in a single embodiment is beneficial. Similar components are, in principle, designated by the same reference numerals, and a description thereof will be omitted. Detailed calculation formulas and calculation procedures described below may be modified as appropriate according to the configuration of an apparatus to which an exemplary embodiment of the present invention is applied, as well as various conditions. The calculation formulas and procedures are not intended to limit the scope of the present invention the following description.

Subject information acquisition apparatuses according to exemplary embodiments of the present invention include an apparatus using a photoacoustic effect, which irradiates a subject (such as a breast, face, and palm) with light (electromagnetic waves), such as near infrared light, and receives acoustic waves generated in the subject to obtain subject information as image data.

In the case of the apparatus using the photoacoustic effect, the subject information to be obtained may refer to a source distribution of acoustic waves generated by light irradiation, an initial sound pressure in the subject, a light energy absorption density distribution or absorption coefficient distribution derived from the initial sound pressure distribution, or a concentration distribution of substances constituting tissue. Examples of the concentration distribution of substances include an oxygen saturation distribution, a total hemoglobin concentration distribution, and an oxyhemoglobin and reduced hemoglobin concentration distribution.

Characteristic information which is subject information at a plurality of positions may be obtained as a two- or three-dimensional characteristic distribution. The characteristic distribution can be generated as image data indicating the characteristic information inside the subject. As employed herein, acoustic waves typically refer to ultrasound waves and include elastic waves called sound waves and ultrasound waves. Acoustic waves generated by the photoacoustic effect are referred to as photoacoustic waves or light ultrasound waves. An acoustic wave detector (such as a probe) receives acoustic waves generated in the subject.

Figure 1:
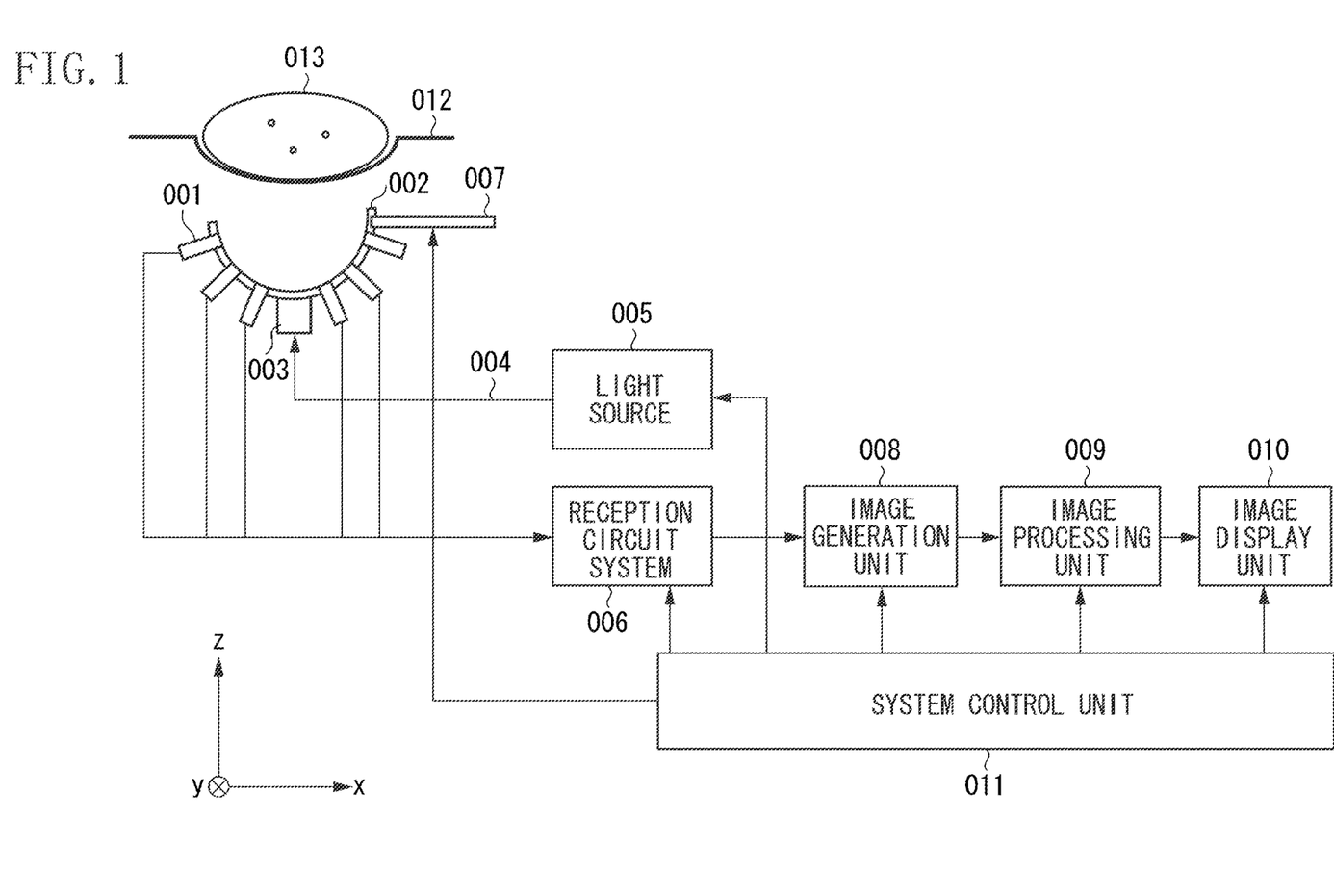
FIG. 1 is a block diagram illustrating a configuration of a subject information acquisition apparatus according to an exemplary embodiment of the present invention.

FIG. 1 is a block diagram illustrating a subject information processing apparatus according to a first exemplary embodiment of the present invention. The subject information processing apparatus according to the first exemplary embodiment includes a support member 002 equipped with a plurality of acoustic wave detection elements 001, an irradiation optical system 003, a transmission system 004, a light source 005, a reception circuit system 006, a sensor array moving mechanism 007, an image generation unit 008, an image processing unit 009, an image display unit 010, a system control unit 011, and a subject holding member 012. The support member 002, together with the acoustic wave detection elements 001 may be expressed as a sensor array 002 in the following.

A probe includes the support member 002 and the plurality of acoustic wave detection elements 001 arranged on the support member 002. The acoustic wave detection elements 001 detect photoacoustic waves propagating from a subject 013 and convert the photoacoustic waves into electrical signals (hereinafter, also referred to as photoacoustic signals). The acoustic wave detection elements 001 may be implemented by using any elements, including ones using a piezoelectric phenomenon, ones using light resonance, and ones using a change in electrostatic capacitance. The acoustic wave detection elements 001 are not limited thereto, and any elements that can receive acoustic waves may be used. In the present exemplary embodiment, the support member 002 has a hemispherical inner surface shape. Acoustic wave detection surfaces of the plurality of acoustic wave detection elements 001 are arranged along the inner surface. The directions of highest reception sensitivity, or directional axes, of the acoustic wave detection elements 001 thus concentrate near the center of the hemisphere. Subject information of higher accuracy can be obtained from the region where the directions of high reception sensitivity of the plurality of acoustic wave detection elements 001 concentrate than from other regions. The support member 002 is not limited to the hemispherical shape. The support member 002 may be shaped like an ellipsoid cut with an arbitrary cross section or configured as a polyhedron as long as the directions of high reception sensitivity of the plurality of acoustic wave detection elements 001 concentrate on a predetermined region. The support member 002 may one- or two-dimensionally support the plurality of acoustic wave detection elements 001. By using such a probe in which the plurality of acoustic wave detection elements 001 is multi-dimensionally arranged, acoustic waves can be simultaneously received at a plurality of positions with reduced measurement time.

As employed herein, a high resolution region refers to a region where reception sensitivity higher than or equal to ½ that at a position of the maximum reception sensitivity, defined by the arrangement of the acoustic wave detection elements 001, is obtained. In the configuration of the present exemplary embodiment, the center of the hemispherical support member 002 is the position of the maximum reception sensitivity. The high resolution region is a spherical region expanding isotropically from the center of the hemisphere.

The light source 005 emits light based on a control signal from the system control unit 011. The shape of the beam of light emitted from the light source 005 is changed by the irradiation optical system 003, and the subject 013 is irradiated with the resulting beam. The light source 005 may generate pulsed light having a pulse width of approximately 10 to 100 nsec. This enables efficient generation of photoacoustic waves. The light source 005 is preferably a laser that produces high output so that the light reaches deep parts of the subject 013. However, this is not restrictive. A light-emitting diode or a flash lamp may be used instead of the laser. Various lasers such as a solid-state laser, a gas laser, dye laser, and a semiconductor laser can be applied as the laser used for the light source 005. The light source 005 preferably generates light having a wavelength such that the light propagates into the interior of the subject 013. For example, if the subject 013 is a living body, the wavelength may be 500 nm or more and not more than 1200 nm. The light source 005 may use a high-output laser of continuously variable wavelength. Examples may include a Nd:YAG-excited Ti:Sa laser and an alexandrite laser. The light source 005 may include a plurality of single-wavelength lasers having different wavelengths.

The light emitted from the light source 005 is transmitted to the irradiation light source 003, which is a light irradiation unit, via the transmission system 004. Optical absorbers in the subject 013 (if the subject 013 is a living body, such as new blood vessels and a cancer) generate photoacoustic waves by absorbing the energy of the light with which the subject 013 is irradiated as described above. Examples of the transmission system 004 may include an articulated arm that includes a plurality of hollow waveguides connected by joints including built-in mirrors so that the light can propagate through the waveguides. Optical elements such as mirrors and lenses may be used to guide and propagate the light through an empty space. The transmission system 004 may include bundled fibers.

The reception circuit system 006 applies sampling processing and amplification processing to reception signals output from the plurality of acoustic wave detection elements 001, converts the reception signals into digital signals, and sends out the digital signals to the image generation unit 008. For example, the reception circuit system 006 includes a signal amplifier such as an operational amplifier, and an analog/digital converter (ADC).

The image generation unit 008 performs image reconstruction processing by using the digital signals sent from the reception circuit system 006. The image reconstruction refers to, for example, processing for calculating an initial sound pressure distribution p(r) of photoacoustic waves in the subject 013 by using filtered back projection (FBP). FBP is an image reconstruction method using, for example, the following equation (1):

$$p(r) = -\frac{1}{2\pi}\int_{S_0}\int \frac{dS_0}{r_0^2}\left[t\frac{\partial p_d(r_0, t)}{\partial t} + 2p_d(r_0, t)\right]_{t=|r-r_0|/c}. \quad \text{Eq. (1)}$$

In the foregoing equation (1), $dS_0$ is a detector size, $S_0$ is the size of an opening used for reconstruction, $p_d(r,t)$ is a signal received by each acoustic wave detection element 001, t is reception time, and $r_0$ is the position of each acoustic wave detection element 001.

The image generation unit 008 sends out reconstruction data generated by performing the foregoing image reconstruction processing to the image processing unit 009. For example, the image processing unit 008 may include a central processing unit (CPU) (including a multicore CPU), a field programmable gate array (FPGA), a workstation, or other pieces of hardware.

The image processing unit 009 performs, for example, gain correction processing on the reconstruction data generated by the image generation unit 008, and applies a Gaussian filter or a median filter to suppress noise components. The image processing unit 009 then generates a maximum intensity projection (MIP) image in a specific direction or a projection image in which color, saturation, and/or brightness are changed depending on a position in a specific direction or a distance from a specific point or plane, and outputs the resulting image as image data. The image processing unit 009 further performs various types of image processing, such as enhancement processing on a region specified by an operator, and sends out image display data to the image display unit 010. The image processing unit 009, together with the system control unit 011, also functions as a display control unit.

The image display unit 010 serves as a user interface and displays the input image display data as a visible image. The image display unit 010 includes a display unit that displays an image. The image display unit 010 may include a touch panel and also serve as an input unit for accepting instructions from a user. The display unit and the input unit may be configured as separate pieces of hardware.

The components described above may be implemented by common pieces of hardware. For example, the image generation unit 008 and the image processing unit 009 may be integrated as a signal processing unit functioning as the image generation unit 008 and the image processing unit 009.

The sensor array moving mechanism 007 serving as a moving unit relatively moves the probe including the support member 002 and the acoustic wave detection elements 001 with respect to the subject 013. Since similar effects can be obtained as long as the relative position between the probe and the subject 013 changes, the subject 013 may be moved with the probe fixed in position. The relative position between the probe and the subject 013 may be changed by moving both the probe and the subject 013. The sensor array moving mechanism 007 includes a movable stage for relatively moving the support member 002 with respect to the subject 013, and can make a two-dimensional relative movement within an x-y plane in the diagram and a three-dimensional relative movement further including the z direction.

Figure 2A:
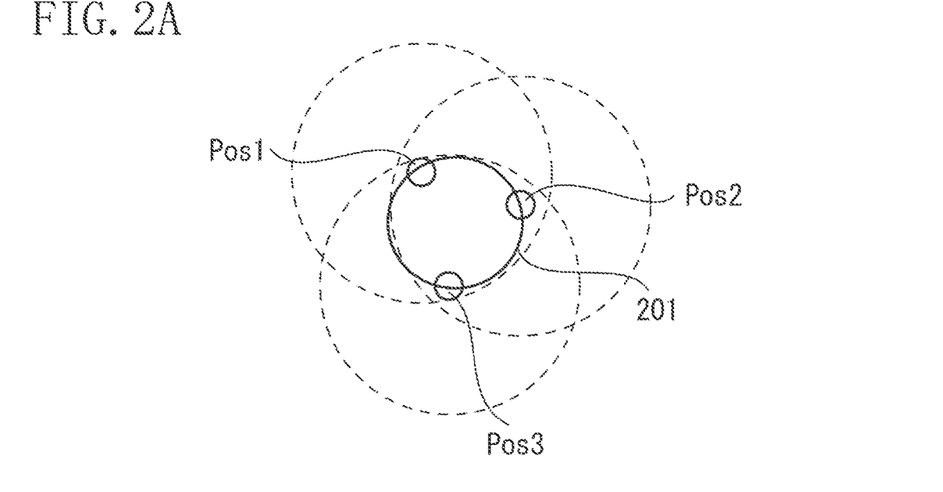
FIGS. 2A and 2B are diagrams illustrating a movement and timing of operation of a probe according to a first exemplary embodiment.

FIG. 2A is a diagram schematically illustrating the movement of the sensor array 002 according to the present exemplary embodiment. FIG. 2A illustrates a trajectory (path) 201 which the center of the high resolution region of the probe traces in a case where the sensor array moving mechanism 007 moves the probe within the x-y plane. In the diagram, positions Pos1, Pos2, and Pos3 represent the positions of the center of the high resolution region at timing Te1, Te2, and Te3, respectively, when the subject 013 is irradiated with light. The dotted-lined circles around positions Pos1, Pos2, and Pos3 schematically indicate the extent of the high resolution regions at the respective positions Pos1, Pos2, and Pos3.

Light irradiation is performed at a plurality of positions where the high resolution regions overlap, and image reconstruction is performed by using the obtained photoacoustic signals. In the high resolution regions, regions of high directionality of many acoustic wave detection elements 001 overlap. The photoacoustic signals generated in such regions can thus be obtained with a high signal-to-noise (SN) ratio. Since the image reconstruction is performed by using the photoacoustic images obtained from locations where the relative position of the sensor array 002 with respect to the subject 013 is different, artifacts on the image obtained by the image reconstruction can be suppressed.

Next, an operation of the image generation unit 008 and the image processing unit 009 will be described. The image generation unit 008 performs image reconstruction by using the photoacoustic signals output from the reception circuit system 006, and outputs the resulting volume data. The image reconstruction is individually performed on the obtained photoacoustic signals upon each light irradiation. The image processing unit 009 combines a plurality of pieces of photoacoustic volume data to calculate combined volume data with suppressed artifacts. The volume data and the combined volume data will hereinafter be referred to also as image data and combined image data, respectively. In the example illustrated in FIGS. 2A and 2B, volume data V1 is obtained by performing light irradiation at timing when the center of the high resolution region is located at the position Pos1, and performing image reconstruction about the space including the dotted-lined high resolution region around the position Pos1 by using the obtained photoacoustic signals. Next, volume data V2 is obtained by performing light irradiation at timing when the center of the high resolution region is located at the position Pos2, and performing image reconstruction about the space including the dotted-lined high resolution region around the position Pos2 by using the obtained photoacoustic signals. Volume data V3 is similarly obtained in the case where the center of the high resolution region is located at the position Pos3.

The image processing unit 009 calculates combined volume data V'1 by combining the three pieces of volume data V1, V2, and V3 while maintaining the relative positional relationship therebetween. In such a manner, a photoacoustic image with suppressed artifacts in the overlapping regions can be obtained from the pieces of volume data V1, V2, and V3. To obtain such an effect, a distance L between at least two of the positions of the center of the high resolution region at points in time when the light irradiation performed preferably satisfies a relationship of L<R. R is the radius of the high resolution region which is schematically assumed to be a spherical or cylindrical region arranged in space.

Image reconstruction can be performed using more photoacoustic signals by controlling the movement of the probe so that the high resolution regions overlap regardless of which position on the path 201 the sensor array 002 is at. This can provide a photoacoustic image with even suppressed artifacts. Such an effect can be obtained, for example, by controlling the movement of the probe to satisfy a relationship of Rrot<R, where Rrot is the radius of the circular path 201. If the movement of the probe is controlled to satisfy a relationship of Rrot<R/2, the high resolution regions overlap in the entire area inside the circulating path. A photoacoustic image in which artifacts are suppressed in an even wider range can thus be obtained.

Figure 2B:
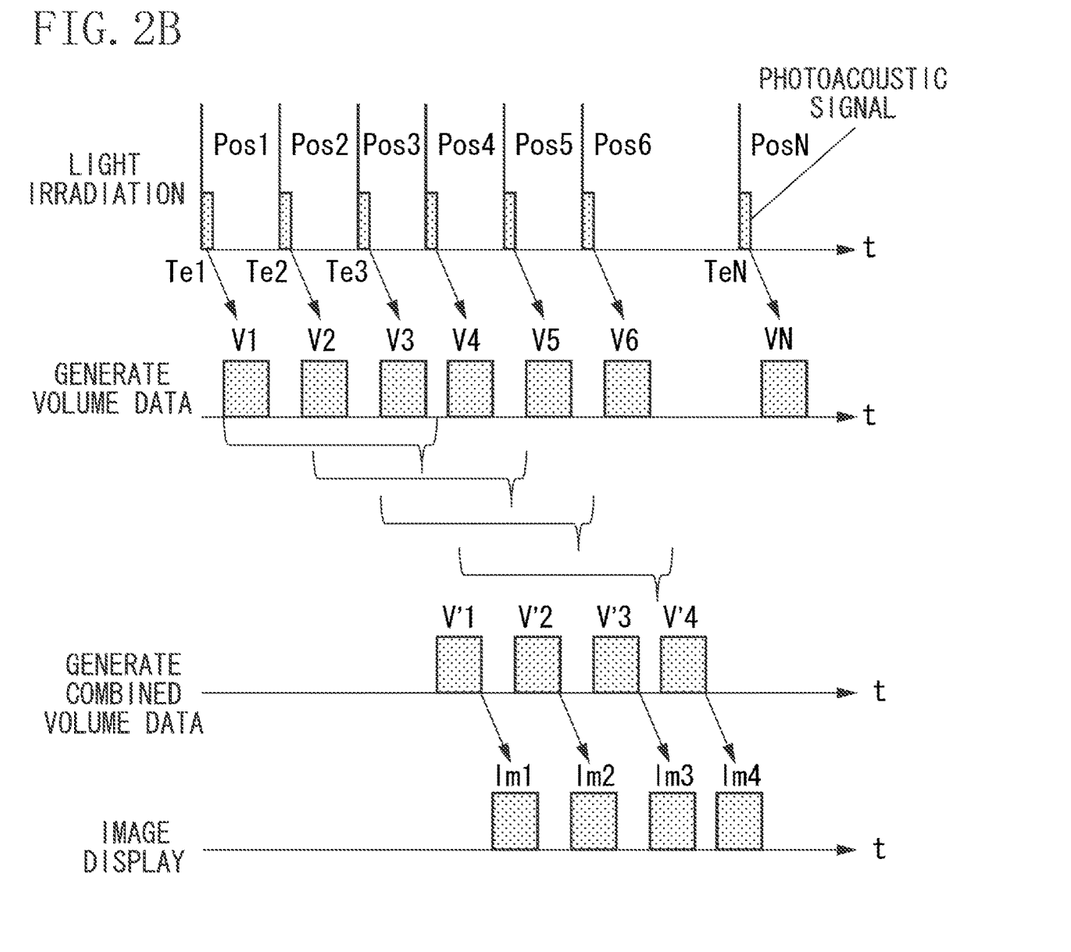

FIG. 2B is a timing chart illustrating the timing of light irradiation. As illustrated in FIG. 2B, light irradiation is performed at temporally equal intervals while the position of the sensor array 002 changes from Pos1 to Pos2, Pos3, . . . , PosN. The reception circuit system 006 obtains photoacoustic signals at each timing. By image reconstruction using the obtained photoacoustic signals, the image generation unit 008 generates volume data V1, V2, . . . , VN. The image processing unit 009 calculates combined volume data V'1 by using the three pieces of volume data V1 to V3. In the present example, combined volume data V'n is generated by combining volume data Vn to V(n+2).

The image display unit 010 can present a photoacoustic image updated in real time by sequentially displaying images according to the combined volume data V'n thus obtained. Since the pieces of volume data to be combined are generated by receiving photoacoustic waves at positions where the high resolution regions overlap, images in which artifacts are suppressed at the overlapping positions in particular can be generated.

Combined volume data is, in other words, the combination of photoacoustic signals obtained during three light irradiations. If the subject 013 is a living body, the imaging object may move due to a body movement such as breathing. If combined volume data is generated by using photoacoustic signals obtained before and after a body movement, the resulting image blurs due to the body movement. The number of photoacoustic volumes used for combination by the image processing unit 009 is, then, preferably limited to a number such that the image is not much affected by the blur. For example, if the body movement due to breathing has a frequency of approximately 0.3 Hz (period of approximately 3.33 seconds), an image with a reduced effect of body movement can be obtained by using photoacoustic signals obtained during a time shorter than the period. Suppose that the frequency of the light irradiation is 10 Hz. If the number of pieces of volume data used for combination is limited to 16 or less, the photoacoustic signals to be used for combination can be obtained within 1.6 seconds. This enables combination in approximately one half the period of the body movement or less. If the number of pieces of volume data used for combination is limited to eight or less, the photoacoustic signals to be used for combination can be obtained within 0.8 seconds, and combined volume data can be obtained by using photoacoustic signals obtained in a period of approximately ¼ that of the body movement. The smaller the number of pieces of volume data used to generate combined volume data is, the higher the temporal resolution of the obtained image is. On the other hand, the greater the number of pieces of volume data used to generate combined volume data is, the higher the SN ratio of the obtained image is. The operator may be allowed to arbitrarily set the number via a not-illustrated input unit. The operator's convenience can be improved by displaying the number of pieces of volume data used for combination. An acquisition time width of the photoacoustic signals used for combination and a frequency (Hz) that can be calculated from the acquisition time width may be displayed so that the operator can recognize the temporal resolution of the obtained image. This facilitates the operator specifying the number of pieces of volume data to be used for combination and the temporal resolution.

According to the foregoing operation, the reception data obtained at the position Pos2 is included in images Im1 and Im2 but not an image Im3. The photoacoustic signals obtained at the position Pos3 are included in the images Im1, Im2, and Im3, but not an image Im4. In other words, the degree of contribution of the photoacoustic signals obtained at a certain position, or the volume data using the photoacoustic signals, to the image displayed on the image display unit 010 decreases with the lapse of time. This enables updating the image while suppressing artifacts by the combination of volume data and suppressing the contribution of temporally old photoacoustic data to the image.

The foregoing operation will be described in general terms. In the present exemplary embodiment, photoacoustic signals are obtained at N (N is an integer of 3 or more) locations of different relative positions with respect to the subject 013, whereby N pieces of volume data are obtained. At least two of ith to (i+m)th pieces of volume data (i+m<N; both i and m are natural numbers) are combined to generate first combined volume data. At least two of (i+n)th to (i+n+m)th pieces of volume data (n is a natural number) are combined to generate second combined volume data. Then, a first combined image and a second combined image are sequentially displayed by updating an image based on the first combined volume data with an image based on the second combined volume data.

As illustrated in FIG. 2A, the probe circulates around a predetermined region (in the present example, the center of the path 201) repeatedly while receiving photoacoustic signals, and images obtained by combining a plurality of pieces of volume data are displayed in succession. This enables the operator to view a moving image of the predetermined region. The moving image may be stored in the image processing unit 009 or a not-illustrated storage unit.

In generating combined volume data from volume data, weights may be assigned to the ratios of combination. For example, in generating combined volume data by using volume data V(i) to V(i+m), the contribution of old reception data to the combined volume data can be further reduced by setting the ratios $\alpha(i)$ to $\alpha(i+m)$ of the respective pieces of volume data V(i) to V(i+m) so that: $\alpha(i) \leq \alpha(i+1) \leq \alpha(i+2) \leq \alpha(i+3) \ldots \leq \alpha(i+m)$.

The image display unit 010 may display the time width needed to obtain the volume data used to generate the combined image data (for example, the period from the timing when the photoacoustic signals are obtained at the position Pos1 to the timing when the reception signals are obtained at the position Pos3). This enables the operator to find out what level of temporal resolution the currently-displayed combined image data has.

The values of the ratios $\alpha(i)$ to $\alpha(i\ m)$ of the respective pieces of volume data in generating the combined volume data may be displayed. The operator may be allowed to change the values, whereby adjustments according to the temporal resolution and the suppression level of artifacts desired by the operator can be made.

The image processing unit 009 may provide an enhanced display of the region corresponding to the high resolution region in the image displayed on the image display unit 010, compared to the other regions.

The present exemplary embodiment is also applicable if a plurality of light sources capable of emitting light of respectively different wavelengths is included or if a single light source of variable wavelength is used as the light source 005. For example, if the wavelength of the light with which the subject 013 is irradiated is switched upon each pulse light irradiation, image reconstruction may be performed by using photoacoustic images obtained by the irradiation of light of different wavelengths or by using photoacoustic images obtained by the irradiation of light of the same wavelength. In either case, at least two of the high resolution regions at the plurality of acquisition timings of the photoacoustic signals preferably overlap. By using only the photoacoustic images obtained by the irradiation of light of the same wavelength, artifact-reduced photoacoustic images specific to the wavelength can be obtained. If the photoacoustic signals having the same wavelength of light irradiation are used, photoacoustic images of high temporal resolution can be provided by using photoacoustic signals obtained at close timings.

In the present exemplary embodiment, combined volume data is generated from a plurality of temporally successive pieces of volume data. However, all of the successive pieces of volume data do not necessarily need to be used. For example, suppose that a light source that can emit light at high repetition frequencies, such as a light-emitting diode, is used. In such a case, using all the plurality of successive pieces of volume data results in an enormous amount of data. The capacity of the storage unit and the load of the image processing unit 109 can be reduced by thinning out some of the pieces of volume data and generating combined volume data from the thinned volume data.

The number of pieces of volume data to be used to generate combined volume data and the ratios of the respective pieces of volume data in generating the combined volume data from the pieces of volume data may be stored as preset values in a storage unit in the system, for example, one included in the system control unit 011. The system control unit 011 then may set appropriate values among the preset values, for example, according to information about the diagnostics department or the part to be observed. The system control unit 011 may refer to patient information such as an input patient identifier (ID), and if the same patient is imaged again, display the same settings as the last time as a candidate. The system control unit 011 may automatically select the same settings.

Figure 3A:
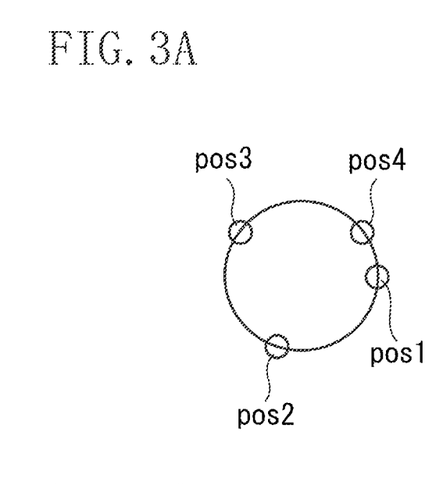
FIGS. 3A, 3B, 3C, and 3D are diagrams illustrating how the probe according to the first exemplary embodiment moves.
Figure 3B:
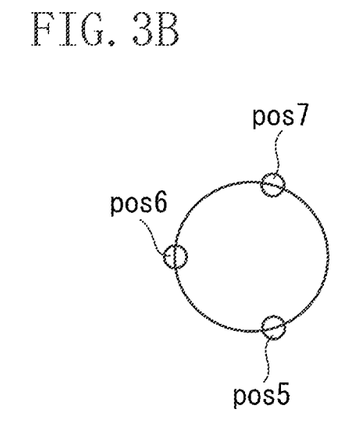
Figure 3C:
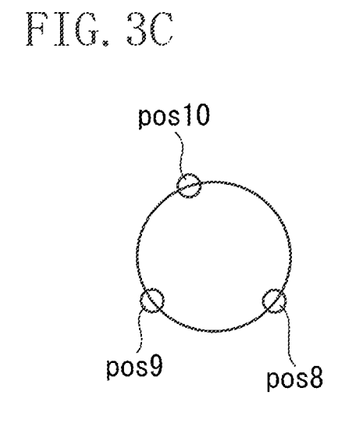
Figure 3D:
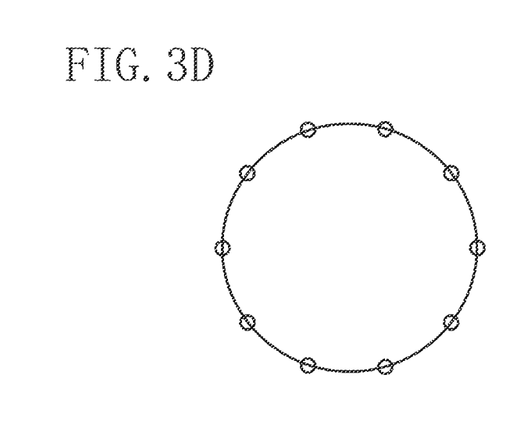

FIGS. 3A to 3D are diagrams schematically illustrating the center positions of the high resolution regions at timings of light irradiation in a case where the repetition frequency of the light irradiation is 10 Hz and the repetition frequency at which the sensor array 002 circulates along the circulating path (in the present exemplary embodiment, the circular path 201) is 3 Hz. The sensor array 002 moves along the circular path 201 clockwise in the diagrams. As illustrated in FIG. 3A, after light irradiations are performed at the positions Pos1, Pos2, Pos3, and Pos4 for the sensor arrays 002 to pass, the sensor array 002 passes the location that previously is the position Pos1 to enter the second round of the circular path 201. In the second round, as illustrated in FIG. 3B, subsequent light irradiations are performed at positions Pos5, Pos6, and Pos7. The sensor array 002 further passes the position that previously is the position Pos1 to enter the third round. In the third round, as illustrated in FIG. 3O, light irradiations are performed at positions Pos8, Pos9, and Pos10. FIG. 3D illustrates the positions Pos1 to Pos10 in an overlapping manner. The relative positions of the sensor array 002 with respect to the subject 013 when the subject 013 is irradiated with light in each round thus differ from one round to another. If the irradiation positions in at least two consecutive rounds are controlled to not overlap with each other, an artifact suppression effect can be obtained by performing image reconstruction using not only the photoacoustic signals obtained at a plurality of positions in the first round (positions Pos1, Pos2, Pos3, and Pos4) but also the photoacoustic signals obtained at a plurality of positions in the second round (positions Pos5, Pos6, and Pos7).

In the example illustrated in FIGS. 3A to 3D, the sensor array 200 returns to the position Pos1 at the eleventh light irradiation. The relative position of the sensor array 002 with respect to the subject 013 thus varies during ten consecutive light irradiations. A photoacoustic image with suppressed artifacts can be obtained by performing image reconstruction using the photoacoustic signals of the ten consecutive light irradiations.

In the present exemplary embodiment, the repetition frequency of the light irradiation is described to be 10 Hz, and the repetition frequency of the circulation of the sensor array 002 to be 3 Hz. However, similar effects can be obtained, for example, if the repetition frequency of the light irradiation is 10 Hz and the repetition frequency of the circulation of the sensor array 002 is 4 Hz, since the relative position between the subject 013 and the sensor array 002 at light irradiation time varies in at least two consecutive rounds of circulation. To change the relative position between the subject 013 and the sensor array 002 at the time of light irradiation for each round, the relationship between the repetition frequency of the light irradiation and the repetition frequency of the circulation can be other than integer multiples. If both the frequencies are integers and controllable, the frequencies can be relatively prime. If the sensor array 002 is controlled to return to the same position after repeating a predetermined number of rounds of circulation, the number of positions to be stored for the position control of the sensor array 002 can be reduced.

Figure 4A:
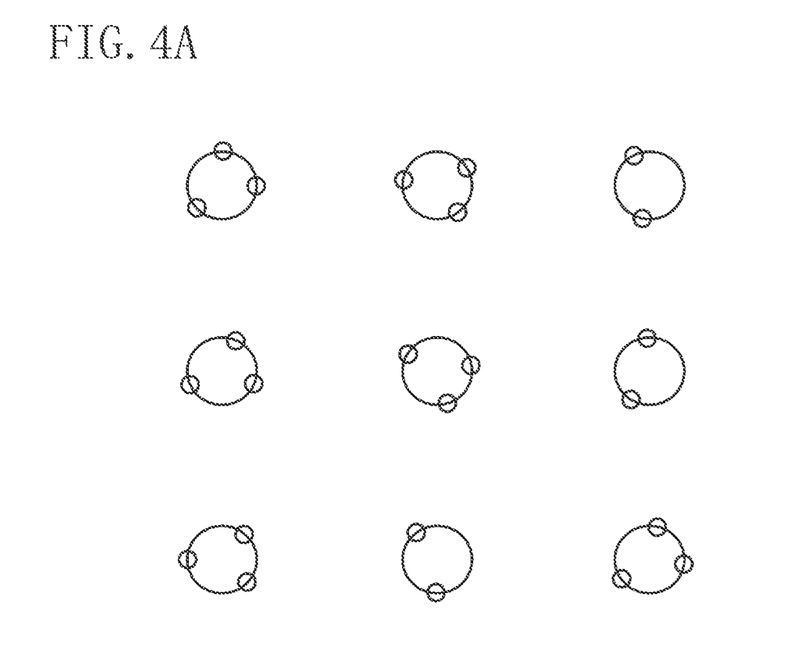
FIGS. 4A and 4B are diagrams illustrating how the probe according to the first exemplary embodiment moves.
Figure 4B:
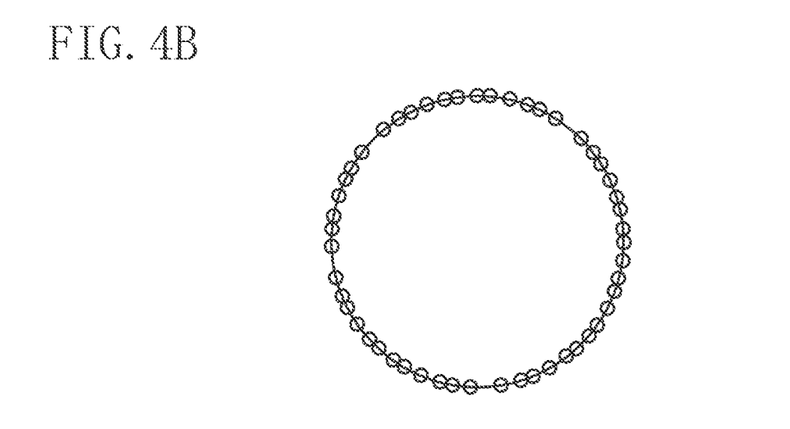

Suppose, for example, that light irradiation is controlled to be performed at every $360°/((1+\sqrt{5})/2)$=approximately 222.5° or 137.5° (=360°−222.5°) on a circular trajectory. In such a case, the relative position between the subject 013 and the sensor array 002 at the time of light irradiation can be made different over repetitive rounds of circulation. This can provide an artifact suppression effect in performing image reconstruction by using photoacoustic signals of many rounds. FIG. 4A illustrates light irradiation positions in up to ninth rounds in a case where the repetition frequency of light irradiation is set to 10 Hz and the repetition frequency of circulation of the sensor array 002 is set to 3.82 Hz so that a light irradiation position comes at every 137.5°. FIG. 4B illustrates all the light irradiation positions in a case where the light irradiation is continued for five seconds. It can be seen that all the light irradiation positions are different. Theoretically, the light irradiation positions can be made different over rounds and rounds of repetition by setting the angle as much as which the position of light irradiation advances between two consecutive light irradiations to a number by which 360° is not divisible, i.e., an irrational number. In actual design, up to how many rounds the light irradiation positions are prevented from coinciding may be appropriately determined by the designer as long as the relative position between the subject 013 and the sensor array 002 at the time of light irradiation varies in at least two consecutive rounds.

Suppose that the circulating path is a circular trajectory with a radius of Rrot, the repetition frequency of light irradiation is FL, and the repetition frequency at which the sensor array 002 circulates along the circulating path is Frot. In such a case, Rrot, Frot, and FL is preferably set to satisfy the relationship:

$$2 \times R\mathrm{rot} \times \sin(F\mathrm{rot}/\mathrm{FL} \times \pi) < R.$$

Figure 5A:
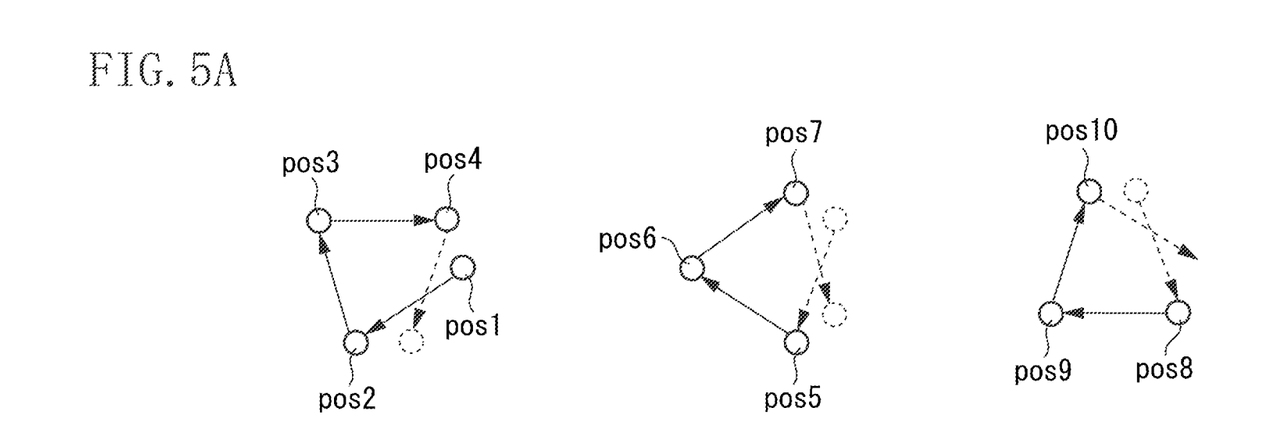
FIGS. 5A and 5B are diagrams illustrating how the probe according to the first exemplary embodiment moves.
Figure 5B:
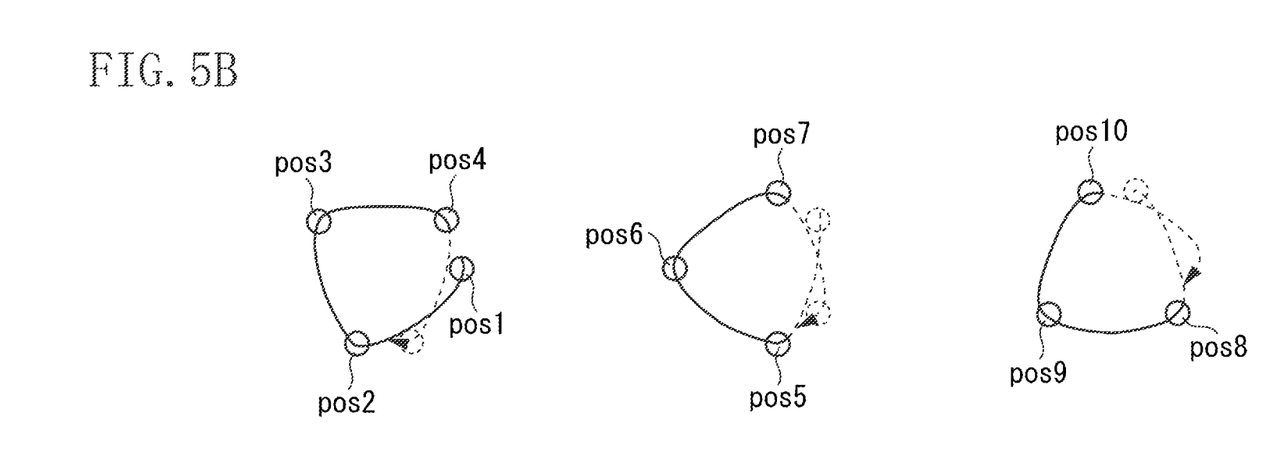
Figure 6:
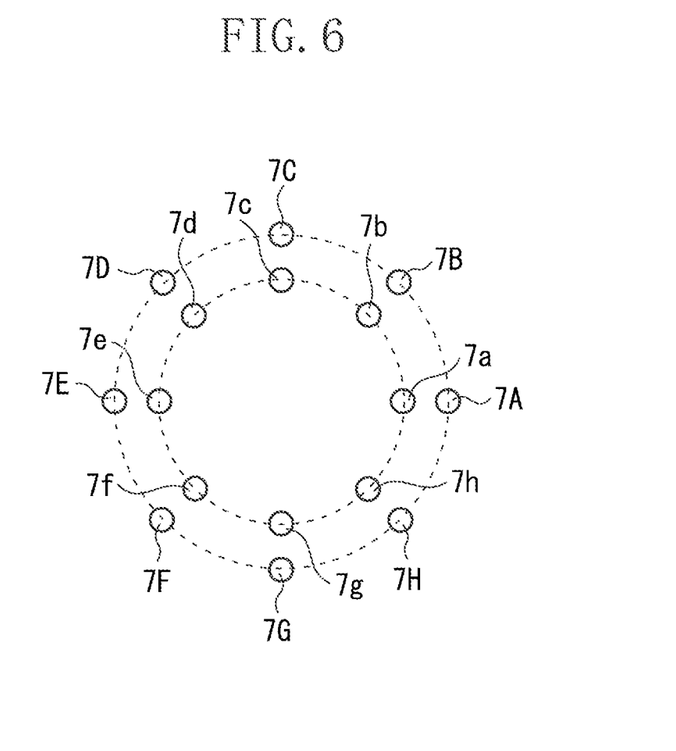
FIG. 6 is a diagram illustrating how the probe according to the first exemplary embodiment moves.

Up to this point, the circulating path is described to be a circular one. However, advantageous effects can be obtained if the relative position of the sensor array 002 with respect to the subject 013 at the time of light irradiation varies for each round. For example, as illustrated in FIGS. 5A and 5B, the sensor array 002 may move between the irradiation positions linearly (FIG. 5A) or in a curved manner (FIG. 5B). Linear movements as in FIG. 5A enable the sensor array 002 to move between the irradiation positions by the shortest distances. The feasible range of the foregoing control parameters can thus be expanded since faster circulating movements can be implemented. As illustrated in FIG. 5B, a curved trajectory passing through the light irradiation positions can be used. A curved trajectory enables control such that the moving distances between the light irradiation positions are reduced compared to the circulating path of circular shape, and acceleration changes in changing the moving direction are reduced compared to the moving pattern of FIG. 5A. The circulating path may thus be constituted by straight lines or curved lines. Pentagonal, circular, and elliptical circulating movements can similarly provide advantageous effects. In other words, the movement of the sensor arrays 002 and the timing of light irradiation can be controlled so that when the sensor array 002 is moved for 720° or more about a center point, the positions of the sensor array 002 at which light irradiation is performed during the first 360° movement differ from those of the sensor array 002 at which light irradiation is performed during the second 360° movement. If the distance of the sensor array 002 to the center point here is constant, the sensor array 002 traces a circular trajectory. An elliptical trajectory, a spiral trajectory, or concentric trajectory can be implemented by changing the distance of the sensor array 002 to the center point. FIG. 6 illustrates an example where the distance to the center point is changed during two consecutive 360° movements, between the first 360° movement and the second 360° movement.

FIG. 6 illustrates the circular circulating paths having respective different radii by dotted lines. For example, in actual circulation, the first round through positions 7A, 7B, 7C, 7D, 7E, 7F, 7G, and 7H may be completed before light irradiations are performed at positions 7a, 7b, 7c, 7d, 7e, 7f, 7g, and 7h of a different circulation radius. Controlling the radius of the circulating path to change for each round in such a manner can make the relative positions of the sensor array 002 with respect to the subject 013 different for each round. In FIG. 6, the first round may be completed through positions 7A, 7D, and 7G, followed by the second round through positions 7B, 7E, and 7H, the third round through positions 7C, 7F, and 7a, the fourth round through positions 7d and 7g, the fifth round through positions 7b, 7e, and 7h, and the sixth round through positions 7c, 7f, and 7A. In such a manner, the radius of the circulating path may be more frequently changed for each round and the relative direction of the sensor array 002 with respect to the vicinity of the center of the circulating paths (area where high resolution regions overlap) may be controlled to vary greatly between light irradiations. This can be expected to suppress more artifacts even with a small number of times of averaging.

Next, a second exemplary embodiment will be described. The second exemplary embodiment differs from the first exemplary embodiment in using a linear probe in which, unlike the sensor array 002 described in the first exemplary embodiment, reception elements are one-dimensionally arranged.

Figure 7:
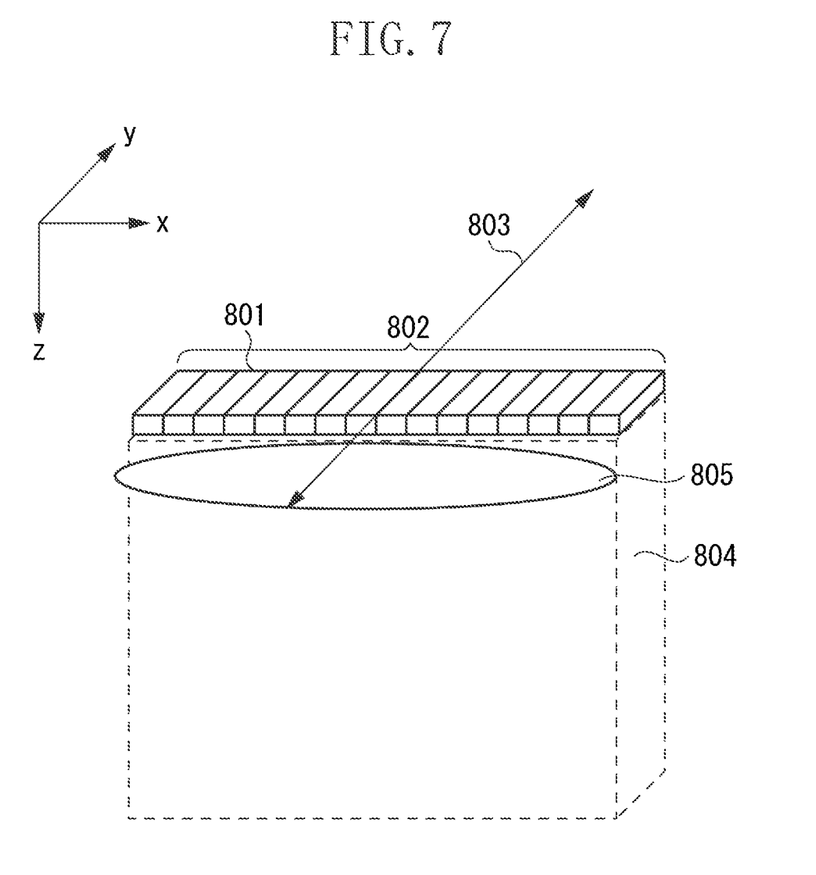
FIG. 7 is a diagram illustrating a configuration example of a probe according to a second exemplary embodiment.

As illustrated in FIG. 7, a linear probe 802 according to this exemplary embodiment includes reception elements 801 which are linearly arranged in an X-axis direction. A sensor array moving mechanism 007 reciprocates the linear probe 802 along a circulating path 803 that is straight in a Y-axis direction. As employed herein, the reciprocal movement will be described to be a circulating movement along a linear circulating path. In the case of using the linear probe 802, a high resolution region is a region where the directionalities of acoustic lenses provided on the plurality of reception elements 801 concentrate, in addition to the array of reception elements 801 in the linear probe 802. Again, like the first exemplary embodiment, a region where reception sensitivity higher than or equal to ½ that at a position of the maximum reception sensitivity is obtained will be referred to as a high resolution region. In this exemplary embodiment, for the sake of simplicity, a region that includes the line on which the reception elements 801 are arranged and that extends and has a thickness in a direction perpendicular to the linear probe 802 (in the diagram, Z-axis direction) will be referred to as a high resolution region 804. The high resolution region 804 may be set as a region in which photoacoustic signals can be obtained with high sensitivity. Such a region is calculated from the spreading, inside a subject, of light emitted from a light irradiation system 805 arranged next to the array of reception elements 801 and from the directionalities of the reception elements 801 and the acoustic lenses.

The position of the light irradiation system 805 illustrated in FIG. 7 is not limited to the illustrated position. For example, light irradiation systems 805 may be provided on both sides of the linear probe 802 in the Y-axis direction in the diagram so that the high resolution region 804 is irradiated with light. In the present exemplary embodiment, the light irradiation system 805 is moved by the sensor array moving mechanism 007 while its relative position to the linear probe 802 is maintained. A method for signal processing is the same as that of the first exemplary embodiment. A description thereof will thus be omitted.

Figure 8:
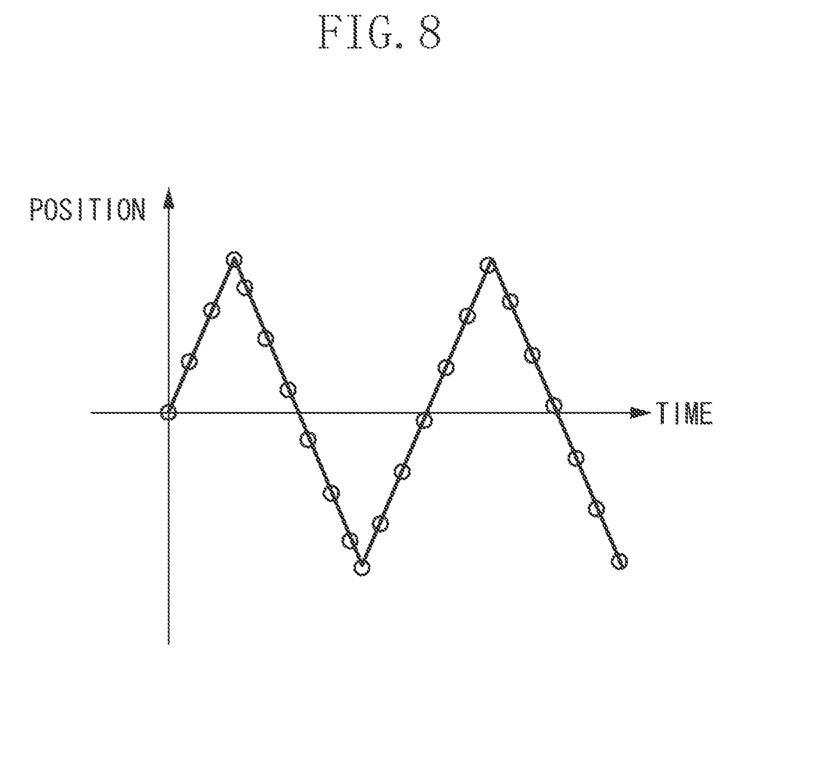
FIG. 8 is a diagram illustrating how the probe according to the second exemplary embodiment moves.

FIG. 8 is a chart illustrating temporal changes of a light irradiation position in the Y-axis direction. The circles illustrated in FIG. 8 represent the positions of the center of the high resolution region 804 on the Y-axis at times when light irradiation is performed. In this exemplary embodiment, the sensor array moving mechanism 007 reciprocates the linear probe 802 and the light irradiation system 805 in the Y-axis direction. In other words, the linear probe 802 and the light irradiation system 805 move along a linear circulating path. As illustrated in FIG. 8, the light irradiation positions during the first reciprocation (i.e., first round) are different from those during the second reciprocation (i.e., second round). In this exemplary embodiment, like the first exemplary embodiment, the light irradiation positions are thus changed between at least two consecutive rounds. A photoacoustic image with suppressed artifacts can therefore be obtained. Again, in this exemplary embodiment, the high resolution regions at two consecutive light irradiations are made to overlap with each other, so that photoacoustic signals with high SN ratios can be obtained from the portion where the high resolution regions overlap. Artifacts can thus be reduced, and a photoacoustic image of favorable image quality even in terms of SN ratio can be obtained.

A third exemplary embodiment of the present invention will be described. The third exemplary embodiment uses a probe including a two-dimensional (2-D) array in which reception elements are two-dimensionally arranged. Even in the case of using the 2-D array, a region where reception sensitivity higher than or equal to ½ that at a position of the maximum reception sensitivity, determined by the arrangement of the reception elements, will be handled as a high resolution region.

Even in the case of using the 2D array, an artifact suppression effect can be obtained by controlling the probe to make circulating movements so that irradiation positions in at least two consecutive rounds are different. The path of the circulating movements may be the circular path described in the first exemplary embodiment or the linear path described in the second exemplary embodiment. In either case, the high resolution regions at two consecutive light irradiations are made to overlap with each other, so that photoacoustic signals of high SN ratio can be obtained from the portion where the high resolution regions overlap. Artifacts can thus be reduced, and a photoacoustic image of favorable image quality even in terms of SN ratio can be obtained.

Other Exemplary Embodiments

Some of the components of the foregoing exemplary embodiments may be extracted and combined without departing from the technical concept of the present invention. For example, the linear probe 802 described in the second exemplary embodiment may be moved to circulate along the circular path described in the first exemplary embodiment.

In the foregoing exemplary embodiments, the irradiation optical system 003 and the probe are described to be integrally moved. However, for example, the physical position of an irradiation optical system may be fixed by using the irradiation optical system that can change the direction of light to be emitted.

According to the foregoing exemplary embodiments, a subject information acquisition apparatus capable of obtaining a photoacoustic image with reduced artifacts can be provided.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD™, a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-118995, filed Jun. 16, 2017, which is hereby incorporated by reference herein in its entirety.

What is claimed is:

1. A subject information acquisition apparatus comprising:
   a light irradiation unit configured to irradiate a subject with light;
   a probe configured to receive an acoustic wave generated in the subject due to irradiation with the light and output a reception signal;
   a moving unit configured to change a location of the probe with respect to the subject in a circulating manner in a common circulating path repeatedly;
   an image generation unit configured to perform image processing including a processing of an image reconstruction to generate photoacoustic image data based on the reception signal;
   an input unit configured to specify a combining number in association with an amount of the plurality of pieces of the photoacoustic image data to be combined based on an input from an operator;
   an image processing unit configured to perform a processing of combining a plurality of pieces of the photoacoustic image data in association with a plurality of locations of the probe to generate a display image data including a combined volume data, in which a number of location is in association with a specified combining number; and
   a control unit configured to control the moving unit, the light irradiation unit, and the image processing unit,
   wherein the control unit is configured to control the moving unit where any one of a plurality sets of the locations in association with an event number of irradiations in an (n+1)th circulating round movement is not to be in accordance with any one of the plurality sets of the locations in association with an event number of irradiations in an nth circulating round movement, where n is a natural number larger than or equal to 1, and
   wherein the image processing unit generates the display image data including the specified combining number to display on the display unit.

2. The subject information acquisition apparatus according to claim 1, wherein the probe includes a plurality of acoustic wave detection elements each configured to detect the acoustic wave and generate an electrical signal, and a support member configured to support the plurality of acoustic wave detection elements so that directional axes of the plurality of acoustic wave detection elements concentrate at a predetermined region.

3. The subject information acquisition apparatus according to claim 2, wherein the control unit is configured to move the probe so that a couple of high resolution regions, which are defined by the concentration of the directional axes of the plurality of acoustic wave detection elements, partially overlap at two consecutive light irradiations.

4. The subject information acquisition apparatus according to claim 1, wherein the circulating round movements are performed repeatedly along a common circular path.

5. The subject information acquisition apparatus according to claim 1, wherein the common circulating path is a circle like shaped path.

6. The subject information acquisition apparatus according to claim 1, wherein the subject is irradiated with the light during a first movement along the path differs from the relative position of the probe with respect to the subject when the subject is irradiated with the light during a second movement along the path successively performed after the first movement along the path, wherein the image processing unit is configured to generate image data on the subject by using a plurality of signals based on the acoustic wave detected by the probe at a plurality of positions during the first circulating round movement along the common circulating path and a plurality of signals based on the acoustic wave detected by the probe at a plurality of positions during the second circulating round movement along the common circulating path.

7. The subject information acquisition apparatus according to claim 1, further comprising a display control unit configured to display an image based on the image data on a display unit.

8. The subject information acquisition apparatus according to claim 1, wherein the light irradiation unit is optically coupled to a light source.

9. The subject information acquisition apparatus according to claim 1, wherein the image processing unit is configured to obtain information in association with an acquisition time period and generate the display image data including the acquisition time period.

10. The subject information acquisition apparatus according to claim 1, wherein the image processing unit is configured to obtain information in association with a cycle period of an acquisition time based on the acquisition time period and generate the display image data including the cycle period of the acquisition time.

11. The subject information acquisition apparatus according to claim 1,
wherein the probe includes a hemispherical transducer array including a plurality of transducers and a hemispherical support member which concentrate their own directional axes for each other and form an effective detection region as a spherical region expanding isotropically from a center of the hemispherical transducer array, and
wherein the control unit is configured to control the moving unit where at least three of the effective detection regions sequentially overlap for each other to form a common reception region.

12. A subject information acquisition apparatus comprising:
a light irradiation unit optically coupled to a light source and configured to irradiate a subject with light;
a transducer configured to receive an acoustic wave propagated from the subject and output a reception signal;
a moving unit configured to change a location of the transducer with respect to the subject in a circulating manner along a common circulating path repeatedly;
an image generation unit configured to perform image processing including a processing of an image reconstruction to generate photoacoustic image data based on the reception signal;
an input unit configured to specify a combining number in association with an amount of the plurality of pieces of the photoacoustic image data to be combined based on an input from an operator;
an image processing unit configured to perform a processing of combining a plurality pieces of the photoacoustic image data in association with a plurality of locations of the transducer to generate combined volume data, in which a number of locations is in association with the specified combining number and output the display image data based on the combined volume data to a display unit, and
a control unit configured to control the moving unit, the light irradiation unit, and the image processing unit,
wherein the control unit is configured to control the location of the transducer where any one of a plurality of sets of the locations in association with an even number of irradiation in an (n+1)th circulating round movement is to be different from any one of a plurality sets of the locations in association with an even number of irradiations in an nth circulating round movement where an artifact component included in the moving image of the subject is going to be reduced, where n is a natural number larger or equal to 1, and
wherein the image processing unit generates the display image data including the specified combining number to display on the display unit.

13. The subject information acquisition apparatus according to claim 12, wherein the common circulating path is a circle like shaped path.

14. The subject information acquisition apparatus according to claim 12, wherein the image processing unit is configured to obtain information in association with an acquisition time period and generate the display image data including the acquisition time period.

15. The subject information acquisition apparatus according to claim 12, wherein the image processing unit is configured to obtain information in association with a cycle period of an acquisition time based on the acquisition time period and generate the display image data including the cycle period of the acquisition time.

16. The subject information acquisition apparatus according to claim 12,
wherein the transducer is secured a spherical support member to form a hemispherical transducer array and form an effective detection region as a spherical region expanding isotropically from a center of the hemispherical transducer array, and
wherein the control unit is configured to control the moving unit where at least three of the effective detection regions sequentially overlap for each other to form a common reception region.

* * * * *